(12) United States Patent
Brannon

(10) Patent No.: US 12,156,685 B2
(45) Date of Patent: Dec. 3, 2024

(54) MEDICAMENT DELIVERY DEVICE

(71) Applicant: James K. Brannon, Leawood, KS (US)

(72) Inventor: James K. Brannon, Leawood, KS (US)

(*) Notice: Subject to any disclaimer, the term of this patent is extended or adjusted under 35 U.S.C. 154(b) by 181 days.

(21) Appl. No.: 17/690,669

(22) Filed: Mar. 9, 2022

(65) Prior Publication Data
US 2022/0287751 A1 Sep. 15, 2022

Related U.S. Application Data

(60) Provisional application No. 63/158,634, filed on Mar. 9, 2021.

(51) Int. Cl.
A61B 17/88 (2006.01)
A61B 17/00 (2006.01)

(52) U.S. Cl.
CPC ............ A61B 17/8822 (2013.01); A61B 2017/00991 (2013.01)

(58) Field of Classification Search
CPC ............ A61B 17/8816; A61B 17/8822; A61B 2017/00991; A61B 5/1416; A61B 5/150106; A61B 5/150236; A61B 5/150099; A61B 10/025; A61B 10/0283; A61M 1/682; A61M 5/178
See application file for complete search history.

(56) References Cited

U.S. PATENT DOCUMENTS

| | | | | |
|---|---|---|---|---|
| 1,683,877 A | * | 9/1928 | Edblom | A61M 1/3681 604/4.01 |
| 4,335,717 A | * | 6/1982 | Bujan | A61M 5/1408 604/83 |
| 4,838,855 A | * | 6/1989 | Lynn | A61B 5/15003 604/6.12 |
| 4,865,583 A | * | 9/1989 | Tu | A61B 5/150221 604/86 |
| 5,012,818 A | * | 5/1991 | Joishy | A61B 10/025 604/44 |
| 8,430,825 B2 | * | 4/2013 | Mark | A61B 10/0275 606/171 |
| 9,730,740 B2 | * | 8/2017 | Rains | A61L 27/58 |
| 2018/0078243 A1 | * | 3/2018 | Rocha-Singh | A61B 17/1635 |

* cited by examiner

Primary Examiner — Anu Ramana
(74) Attorney, Agent, or Firm — Arthur K. Shaffer; McDowell Rice Smith & Buchanan, P.C.

(57) ABSTRACT

The present invention provides a medicament delivery device configured for delivery of a medicament through a removable cartridge which includes a cylindrical construct configured for receiving a plunger rod at a proximate end with a central chamber having a side portal and an axial end portal in communication with a distal bone delivery end, the side portal extending from the central chamber and configured for receipt of the removable cartridge, the central chamber having a radially extending sidewall which presents an elliptical body and the axial end portal configured for reciprocal receipt of a telescopic plunger, the distal bone delivery end being in communication with the removeable cartridge for distribution of a medicament therethrough.

5 Claims, 2 Drawing Sheets

MEDICAMENT DELIVERY DEVICE

FIELD OF THE INVENTION

The current invention relates in general to an improved cementitious delivery device and method and more specifically to a targeted cementitious delivery device with a pneumatic induction structure in communication with a removable cartridge of cementitious fluid for pneumatic introduction of the fluid into a bone defect.

BACKGROUND OF THE INVENTION

Bone defects often occur as a result of a break, fracture, injury, disease or accident. To help treat these bone defects, various treatments are available including medicines, support structures and or braces are used. In some cases, these bone defects require surgery to repair, replace or support the detected bone defect.

Recently, minimally invasive techniques have been used to treat fractures using image-guided minimally invasive surgical procedures to strengthen fractures. Using a small incision and a special x-ray imaging device along with a biocompatible liquid orthopedic cement, the fracture may be treated by injecting the cement through a needle into the fracture. However, x-ray imaging of the surgical site is limited for non-radiographic material and pressure within the bone can be a barrier for injecting a cementitious material into the fracture site. Aside from these concerns, the cementitious material requires a diseased host bed of bone to act upon it, the non-living cementitious material having never been alive, to promote healing of the fracture. In contradistinction, the material delivered should and must be of a nature so that it will act upon the diseased host bed of bone.

Another minimally invasive treatment for fractures is the balloon-assisted vertebroplasty technique known as balloon kyphoplasty. Using a kyphoplasty procedure a cement-like material is injected directly into the fractured bone; however, kyphoplasty inserts an inflatable balloon between the pieces of a collapsed bone to reposition and support the collapsed bone and compact damaged or soft bone to create a cavity. Once the cavity is created, the balloon is then deflated and orthopedic cement can be injected into the facture. However, once again, pressure from inside the fracture can prevent proper inflation of the balloon or compression of the soft or damaged bone area. Issues can arise from introducing air or gasses into a body cavity, which may be the result of a leak or tear in the balloon. To avoid issues with gasses, some attempts include use of a fluid. However, fluids are generally non-compressible and, thus, have limited use in compressing the damaged or soft bone areas.

Because of the pressure and techniques used to introduce the cementitious material into the bone fracture is difficult, problems can occur with improper control of the quantity of cement delivered to the fracture and the method for delivering the cement can cause the cement to leak into areas outside of the area of treatment which can be dangerous and even fatal to a patient. Notwithstanding the difficulties with delivery of a cementitious material to a fracture site, current systems only provide means for delivering a homogenous substantially liquid medicament in a manner that requires in situ displacement of the bone and soft-tissue.

Some prior attempts include utilizing instruments and pressurized delivery devices which supply an actuating force that acts either directly or through a medium to cause a flowable compound to be delivered from the delivery device to a cannula and into the fracture. However, many of the attempts do not allow for precise control of the cement delivery or of the quantity which is delivered.

Therefore, in view of the prior art, there exists a need for devices and methods that permit effective delivery of cementitious material into a bone defect, such as a fracture, that allows for precision over the quantity and location without causing damage to nearby tissue which at least addresses some of the aforementioned problems. The devices and methods of the present invention address these and other needs that will become apparent to those skilled in the art based on the following specification and the accompanying drawings.

SUMMARY OF THE INVENTION

A medicament delivery device configured for delivery of a medicament, said medicament delivery device comprising a removable cartridge presenting a cylindrical construct configured for receiving a plunger rod at a proximate end and a threaded distal end; a central chamber having a side portal and an axial end portal in communication with a distal bone delivery end; said side portal extending from said central chamber and configured for receipt of said removable cartridge; a seal presented between said removable cartridge and said distal bone delivery end; said central chamber having a radially extending sidewall which presents an elliptical body; said axial end portal configured for reciprocal receipt of a telescopic plunger; and said distal bone delivery end being in communication with said removeable cartridge for distribution of a medicament therethrough.

DETAILED DESCRIPTION

Certain terminology will be used in the following description for convenience in reference only and will not be limiting. For example, top, bottom, front, back, right and left refer to the illustrated embodiment as oriented in the view being referred to. The words "upwardly" and "downwardly" refer to directions up or down and away from, respectively, the geometric center of the embodiment being described and designated parts thereof. Such terminology will include the words specifically mentioned, derivatives thereof and words of similar meaning.

Figure 1:
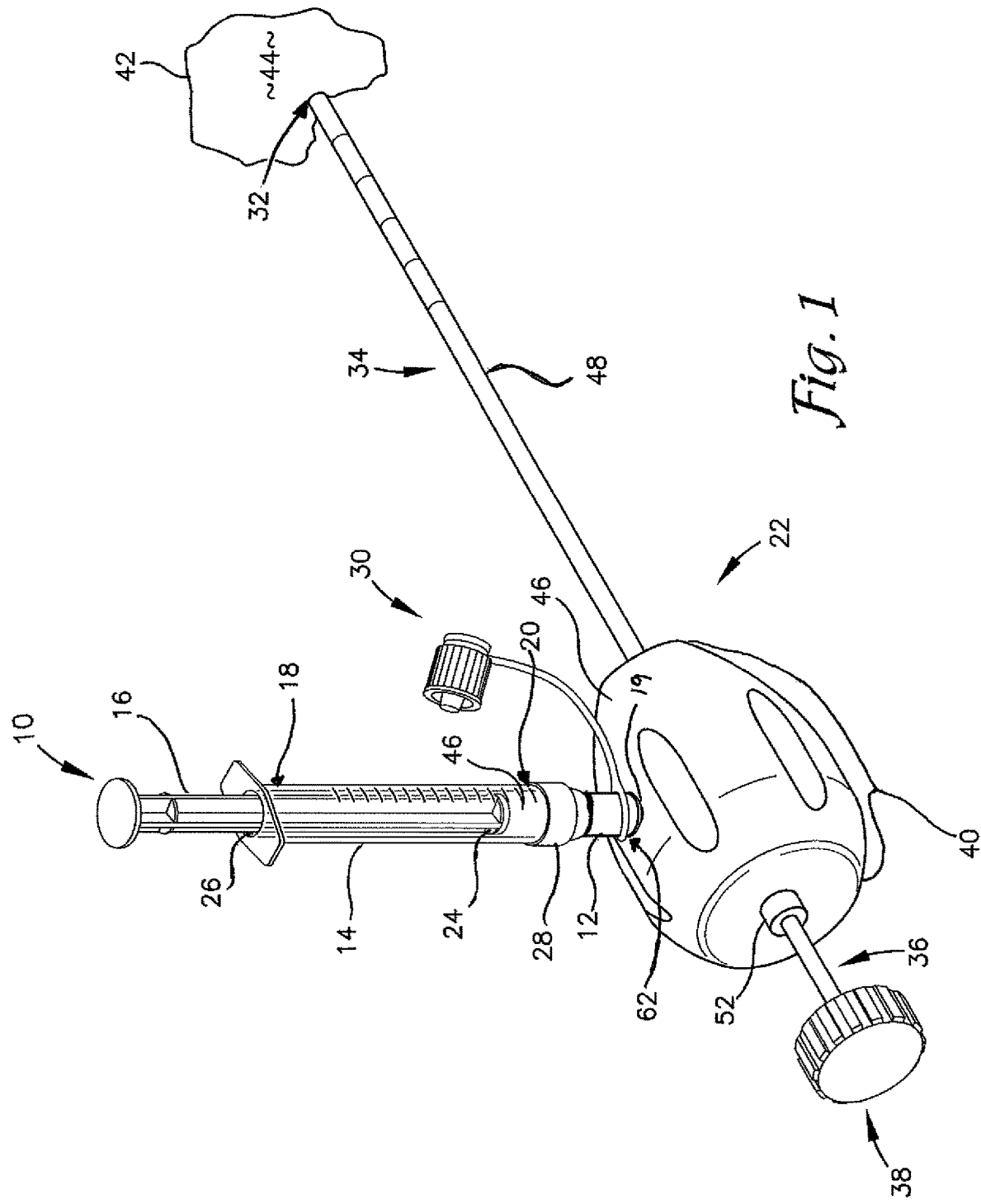
FIG. 1 is side perspective view of the medicament delivery device in receipt of a removable cartridge.
Figure 2:
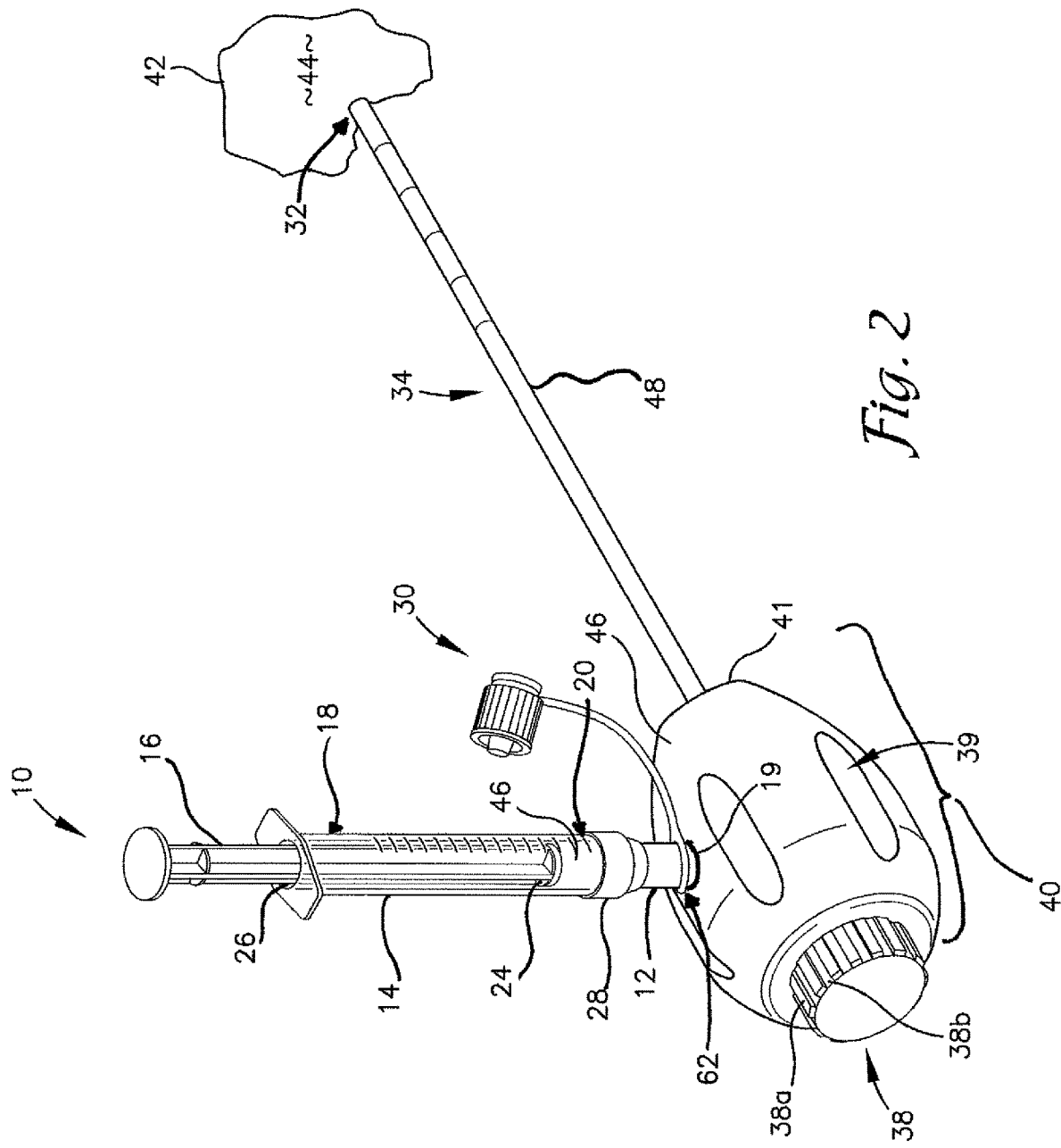
FIG. 2 is side perspective view of the medicament delivery device of FIG. 1 with a plunger rod fully inserted into a central body.

Referring to FIG. 1, a removable cartridge device referred to by reference numeral 10 is illustrated as being in communication with a medicament delivery device shown generally at 22. The medicament delivery device 22 is generally of a size and shape to contain a medicament 46 therein. In the depicted embodiment of FIG. 1, the medicament delivery device generally includes a central chamber 40 with a side portal 12 and an axial end portal 52 generally spaced longitudinally across the central chamber.

The central chamber 40 is includes a contoured surface which is generally elliptically shaped with a radially extending sidewall. As depicted, the elliptical sidewall includes a plurality of radially spaced, depending elliptical contours 39.

As depicted, the elliptical contours 39 extends longitudinally along the central chamber 40. Generally, each of the elliptical contours 39 is circumferentially spaced along the central chamber 40 between a proximal receiving end 41 and an axial end portal 52. The contoured surface associated with the central chamber 40 and elliptical contours 39 presents a frictional surface for an improved fit and more secure grip during use. In addition, the central chamber 40 provides a communication pathway between the side portal 12 and a distal end 20.

The removable cartridge device 10 generally includes a plunger rod 16 having at its distal end a piston 24. The plunger rod 16 is telescopically positioned within a cylindrical construct 14. The piston 24 is in hermetic communication with an inner wall 26 of the cylindrical construct.

The cylindrical construct 14 extends from a proximate end 18 to a distal end 20, the distal end 20 having a threaded or grooved end configured for receiving a securing cap 28 located at the distal end 20 and having an internal passage extending therebetween. The distal end 20 is in hermetic and stable communication with a side portal 12. In general, the distal end 20 is configured to allow the unobstructed flow of the medicament 46 from the cylindrical construct 14 and into a central chamber 40. Once the medicament 46 is received from the cylindrical construct 14 it flows through a hollow tube 34 extending from the central chamber 40 to the bone lesion 44.

The medicament delivery device shown generally at 22 further comprises a tethered cap 30 for alternately closing the side portal 12 when not in use. Further alternately, the tethered cap 30 may be used to close an axial end portal 52 having been configured to hermetically receive said tethered cap 30 when a telescopic plunger 36 is not positioned therein. The medicament delivery device 22 further includes a distal bone delivery end 32 having penetrable means for insertion into a bony host bed 42 having bone lesion 44 into which the medicament 46 may be delivered. The distal bone delivery end 32 is distal to a proximal receiving end 41 by means of the hollow tube 34 having a tubular sidewall 48 with an internal diameter of sufficient dimension to substantially prevent the flow of a fluid therethrough when said telescopic plunger 36 is advanced proximally. More specifically, the telescopic plunger 36 may be advanced proximally by manually retracting said telescopic plunger 36 while securely holding a grippable cap 38 of said telescopic plunger 36.

In general, the grippable cap 38 includes a plurality of upending sections 38a spaced circumferentially along the cap 38. The upending sections 38a present depending spaces 38b between each of the upending sections 38a such that the grippable cap 38 has an increased frictional surface.

Retraction of the telescopic plunger 36, may induce a vacuum within the hollow tube 34. The vacuum may increase in magnitude until a distal telescopic plunger end (not shown) is positioned functionally about a proximal side 62 of the side portal 12. When the distal telescopic plunger end (not shown) is positioned at the proximal side 62, the medicament 46 may flow from the cylindrical construct 14 and into the hollow tube 34 for delivery of the medicament 46 into the bony lesion 44. The medicament 46 may comprise a cementitious material or an all biologic composite. Once the medicament 46 is at least partially contained within the hollow tube 34, the telescopic plunger 36 may be advanced distally inducing the medicament 46 to flow along the sidewall 48 and into the bony lesion 44. The medicament 46 may include but is not limited to bone cement.

The side portal 12 and said axial end portal 52 are generally cylindrical and configured for receipt of a suction device (not shown) or said telescopic plunger 36 as shown in FIG. 1. When the distal end of the telescopic plunger 36 is positioned at the proximal side 62, the medicament 46 may alternatively be induced to flow from the cylindrical construct 14 and into the hollow tube 34 for transport of the medicament 46 for delivery into the bony lesion 44. Retraction of the telescopic plunger 36, may induce a vacuum within the hollow tube 34. The vacuum may increase in magnitude until a distal end of the telescopic plunger 36 is positioned functionally about a proximal side 62 of the side portal 12 and a medicament is induced to flow from the cylindrical construct 14 through the central chamber 40 towards the proximal receiving end 41.

As the telescopic plunger 36 is operated, it generally induces a frictional resistance to a proximal flow of tissue within said host bed 42 along the tubular sidewall 48 which is greater than the frictional resistance of a distal flow of the medicament 46 from within the cylindrical construct 14 and into the hollow tube 34 thereby preferentially allowing the filling of said bony lesion 44 at a low pressure.

Optionally and operationally disposed, the transition between the proximal receiving end 46 of the medicament delivery device 22 and the distal delivery end 32 of the hollow tube 34 having a sealing structure 19 such as an o-ring to present a seal between the telescopic plunger 36 and the tubular inner wall 48 of the hollow tube 34. The sealing structure 19 may be located internally within the central chamber 40, the side portal 12 or it may be located between the side portal 12 and the central chamber 40.

In some cases, the frictional resistance needed to overcome for delivery of the medicament 46 is a direct correlation to the viscosity of the medicament 46. Functionally, the hollow tube 34 has a diameter to substantially prevent the proximal flow of tissue from the host bed 42 allowing the hollow tube 34 to be filled selectively with the medicament 46.

In one embodiment, the medicament 46 may fill the hollow tube 34 in a direction from the proximal end 18 to the distal end 20. In one embodiment, the pressure needed to deliver the medicament 46 into the bony lesion 44 may be substantially reduced. To help reduce the needed pressure, the telescopic plunger 36 may include a distal surface area of a size and dimension that is inverse to the generatable pressure P induced when the telescopic plunger 36 is in motion. This may result in a more precise delivery of the medicament 46 to the bony lesion 44. This may also result in a reduced delivery force necessary to deliver the medicament 46 to the bony lesion 44, improving patient safety.

It should be understood that while certain forms of this invention have been illustrated and described, it is not limited thereto except insofar as such limitations are included in the following claims.

What is claimed and desired to be secured by Letters Patent:

1. A medicament delivery device configured for delivery of a medicament, said medicament delivery device comprising:
    a removable cartridge presenting a cylindrical construct with a proximal end and a distal end, said proximal end configured for receiving a plunger rod;
    a hollow tube extending from a proximal receiving end to a distal bone delivery end;
    an elliptical body having a radially extending sidewall which presents an elliptically shaped central chamber having a side portal and an axial end portal in communication with said distal bone delivery end;

said side portal extending from said central chamber and configured for receipt of said removable cartridge;

a seal positioned between said removable cartridge and said side portal;

said axial end portal configured for reciprocal receipt of a telescopic plunger; and said distal bone delivery end being in communication with said removeable cartridge via the elliptical body for distribution of a medicament therethrough.

2. The medicament delivery device of claim 1 wherein said elliptical body extends from the axial end portal to the proximal receiving end.

3. The medicament delivery device of claim 1 further comprising a sealing structure between the telescopic plunger and the inner wall of the hollow tube whereby a negative pressure is induced at said distal bone delivery end upon rearward movement of said telescopic plunger.

4. The medicament delivery device of claim 1 wherein said telescopic plunger has a grippable cap.

5. The medicament delivery device of claim 1 wherein an exterior surface of said elliptical body includes a plurality of circumferentially spaced elliptical contours.

* * * * *